United States Patent [19]

Smith

[11] Patent Number: 5,123,113
[45] Date of Patent: Jun. 23, 1992

[54] BODY PORTION PROTECTING MEANS

[76] Inventor: Mary E. Smith, 180 Arlington Ave., Hawthorne, N.J. 07506

[21] Appl. No.: 652,948

[22] Filed: Feb. 8, 1991

[51] Int. Cl.⁵ ............................................. A41D 13/00
[52] U.S. Cl. ....................................... 2/2; 2/DIG. 7; 128/892; 5/502
[58] Field of Search ...................... 2/2, 114, 16, 61, 59, 2/22, DIG. 7; 5/61, 81 B, 484, 494, 502, 482, 60; 128/846, 849, 872, 889, 892, 893, 894

[56] References Cited

U.S. PATENT DOCUMENTS

| | | | |
|---|---|---|---|
| 3,216,417 | 11/1965 | Posey | 2/16 |
| 3,648,291 | 3/1972 | Pankers | 2/16 |
| 3,769,642 | 11/1973 | Warman | 5/81 B |
| 3,916,447 | 11/1975 | Thompson | 2/114 |
| 4,536,903 | 8/1985 | Parker | 5/61 |
| 4,571,960 | 2/1986 | Hursh et al. | 2/239 |
| 4,922,551 | 5/1990 | Anthes | 2/69.5 |
| 4,944,053 | 7/1990 | Smith | 5/61 |

FOREIGN PATENT DOCUMENTS

| | | | |
|---|---|---|---|
| 1007768 | 3/1977 | Canada | 5/81 B |
| 2157558 | 10/1985 | United Kingdom | 5/81 B |

*Primary Examiner*—Werner H. Schroeder
*Assistant Examiner*—Amy Brooke Vanatta
*Attorney, Agent, or Firm*—W. Patrick Quast

[57] ABSTRACT

A selective body portion protecting means for use on an elbow, knee, leg, calf, or the like, to prevent friction on a wound, burn, bed sore, or the like. The protector includes a first non-woven fabric which contacts the body portion, and a second frictionless fabric which contacts the first non-woven fabric, and a third frictionless fabric which contacts the second frictionless fabric and which rests on a support. The first and second fabrics typically are formed and joined so as to envelop the selective body portion.

16 Claims, 8 Drawing Sheets

BODY PORTION PROTECTING MEANS

FIELD OF THE INVENTION

The invention generally relates to a body protecting means. In particular, the invention relates to a body protecting means, including: a body portion protector enveloping a body portion, having an inner non-woven fabric and an outer frictionless fabric; and, a frictionless fabric member disposed upon the surface in contact with the particular body portion.

BACKGROUND OF THE INVENTION

One of the most significant problems experienced by patients when confined to a hospital for an extended period is the development of bed sores. Through the continual rubbing of the body contact or pressure points upon the sheet fabric on the bed, these sores develop quickly. Immobilized patients must be turned frequently in order to minimize their occurrence. Even patients that are able to turn themselves must be alert to their development and consciously turn themselves as frequently as is necessary. In many cases, the pain attending the occurrence of bed sores is more intense than the ailment or condition which necessitated the patient's hospitalization. Of course, this problem can occur in any circumstance where a person has to recline, relatively immobilized, on a bed or similar surface, for any extended period of time.

In my recent patent, U.S. Pat No. 4,944,053, I describe a fabric device which is useful in facilitating the movement of a person's body while reclining on a bed, resting surface, examining table, or the like. Therein, I describe a combined fabric device comprising a first and second fabric each including a non-woven, paper-thin, soft and pliable material seamed to a second frictionless material. The second, frictionless material of each of the two fabric devices are disposed adjacent to each other, such that they coact to permit relatively, friction-free movement therebetween. The two fabric devices can be seamed at each end so as to form a closed loop. Or, alternately, the first fabric is disposed co-extensively along the second fabric device, again, such that the frictionless fabrics coact with each other. As described in the aforementioned patent, the combined fabric device is initially positioned beneath the patient's body, so as to extend between the mid-back and thighs. The patient, using his body extremities, including his arms and legs, in conjunction with some lateral hip movement is easily able to rotate his body as required.

Of course, if a patient is totally immobilized, the purposes of the '053 patent are somewhat thwarted. No longer can the patient routinely turn himself, but must rely on hospital staff. Although the device described in the '053 patent does facilitate movement of the patient, whether by himself, or the hospital staff, certain body contact points, for example, the patient's elbows, may be susceptible to the development of bed sores, by their movement on the soft pliable fabric material, although this is less likely to occur because of the texture of that material.

Further, the device described in the '053 patent, for purposes enumerated in that patent, is disposed, between the thighs and mid-back. In this case, the patient's legs would typically be in contact with the linens covering the bed or other resting surface. Thus, they remain susceptible to the development of bed sores.

In addition to the above, often patients are hospitalized because of open wounds or sores on various portions of the body. This could result, obviously, under a variety of circumstances. Also, of course wounds may result from surgery. Thus, it becomes important to isolate those parts of the body which bear these wounds from contact with the resting surface.

It therefore is a primary object of this invention to provide a body protecting means for various portions of the body, so as to preclude the development of bed sores.

It is another object of this invention to provide a fabric body protecting device to isolate open wounds on certain portions of the body, from aggravating contact with the bed surface.

It is yet another object of this invention to provide a fabric protecting device which coacts with the device described in the '053 patent so as to minimize the development of bed sores, or the aggravation of wounds on body members disposed upon the fabric device described in that patent.

SUMMARY OF THE INVENTION

According to the present invention, a fabric body protecting means is provided. This protecting means comprises a body protector enveloping a body portion, which comprises an inner, non-woven fabric and an outer frictionless fabric; and a frictionless fabric member disposed upon the surface in contact with the particular body portion.

The inner, non-woven fabric and outer frictionless fabric are typically fashioned or constructed to enclose a particular body member such as an elbow, foot, leg, etc. The outer frictionless fabric coacts with the frictionless fabric member, disposed upon the resting surface.

The coaction of the outer frictionless fabric and the frictionless fabric member isolate the portion of the body encompassed by the composite body protector to thus prevent the development of bedsores, or exacerbation of existing wounds.

The foregoing and other objects, features and advantages will be apparent from the following description of the preferred embodiments of the invention and as illustrated in the accompanying drawings.

DESCRIPTION OF THE PREFERRED EMBODIMENT

Figure 1:
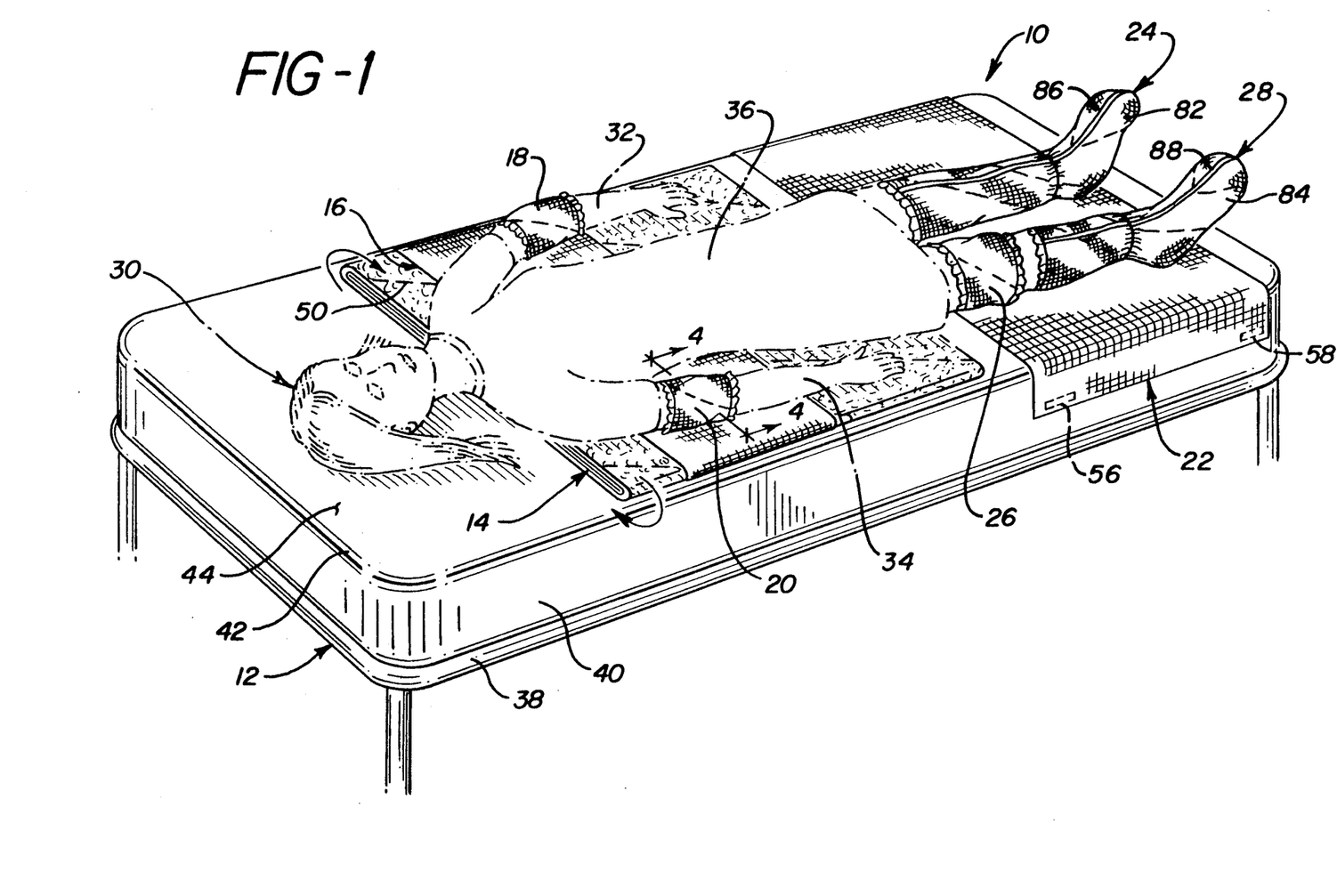
FIG. 1 is a perspective view of some fabric body protecting means according to the invention.

As shown in FIG. 1, an assembly 10 includes a support 12, an upper four-layer roll-type mat 14, an upper low-friction, or frictionless single-layer sheet 16 and left and right elbow protectors 18, 20. Assembly 10 also includes a lower single layer frictionless sheet 22, a leg protector 24, a knee protector 26, and a calf protector 28. A patient 30 rests her left and right arms 32, 34 and her torso 36 on support 12.

As shown in FIG. 1, support 12 has a bed frame 38, and a mattress 40, which has a cover 42 that has a top surface 44.

Figure 4:
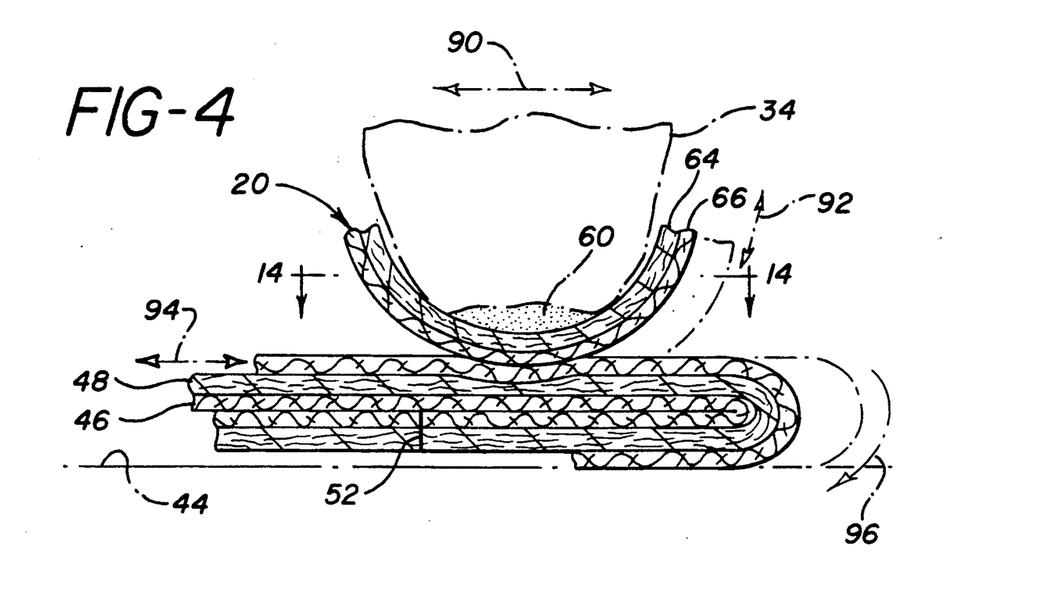
FIG. 4 is a section view as taken on line 4—4 of FIG. 1.

As shown in FIG. 4, mat 14 is a continuous roll or tube or loop. Mat 14 is a single fabric device which is doubled over to form a four-layer mat. Mat 14 includes an inner tubular frictionless fabric 46 and includes an outer tubular non-woven fabric 48. Mat 14 typically also includes diagonal stitching 50 which interconnects fabrics 46, 48. Mat 14 also has a seam 52, which is disposed parallel to support 12. Mat 14 typically would be one of the embodiments of the combined fabric device described in my aforementioned patent.

As shown in FIGS. 1 and 4, frictionless sheet 16 is a nylon fabric strip which is disposed around the loop of mat 14. Lower frictionless sheet 22 is a nylon sheet which has a plurality of connecting means 56, 58 for affixing sheet 22 to mattress 40.

Figure 14:
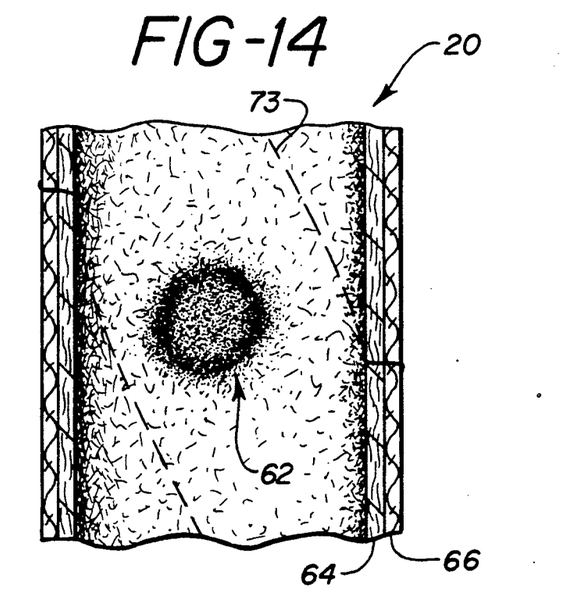
FIG. 14 is a section view as taken on line 14—14 of FIG. 4.

As shown in FIGS. 1, 4, 7, and 8, elbow protector 20 is identical to elbow protector 18 and is similar in section view to leg protector 24, knee protector 26, and to calf protector 28. The various protectors are used in combination with frictionless sheets, such as 16 or 22, to isolate the covered body member from frictional contact with surface 44 to prevent sores from developing. Where sores, burns or wounds already exist, a protector, such as 20, covers the sore, or bed sore, or burn, or wound 60, which may have disposed thereon a salve 62 (FIG. 14). Typically, a protector, such as elbow protector 20 has a first inner, non-woven fabric 64, and has a second outer frictionless fabric 66. Fabrics 64, 66 form a sleeve portion 68, and have left and right end elastic bands 70, 72. Sleeve portion 68 has diagonal stitching 73, which interconnects fabrics 64, 66. Fabrics 64, 66 are substantially identical to respective fabrics 48, 46.

Figure 8:
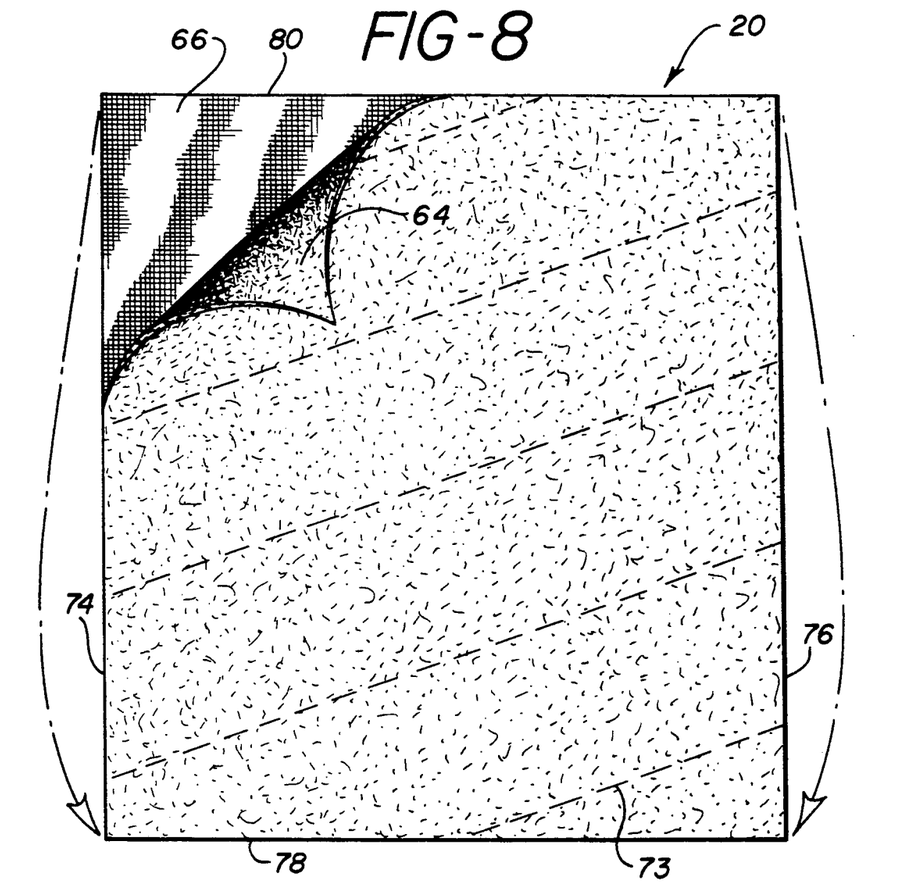
FIG. 8 is a developed view of the fabric body protector as shown in FIG. 7.
Figure 13:
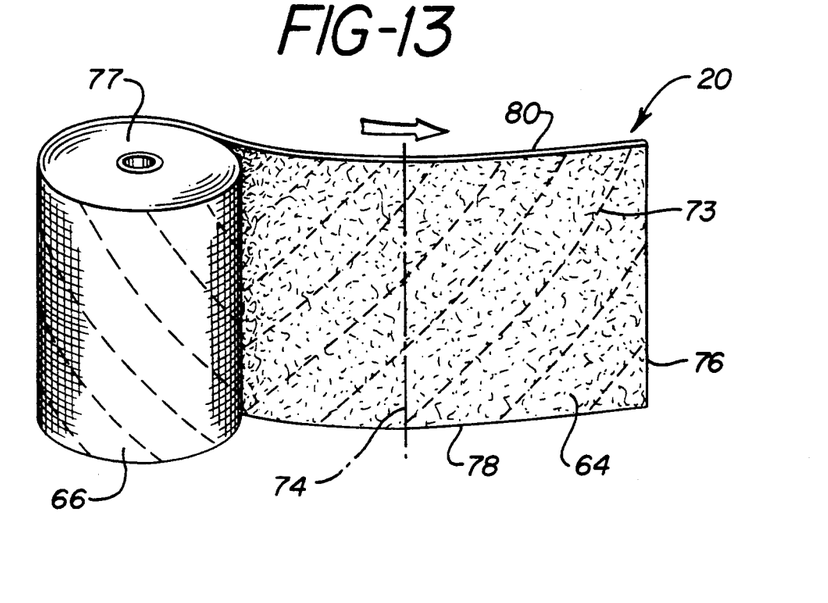
FIG. 13 is a perspective view of a roll of developed protectors, like the developed protector of FIG. 7.

As shown in FIGS. 8 and 13, protector 20 has left and right end edges 74, 76, which are cut from a roll 77, and also has bottom and top seam edges 78, 80. Either of the edge pairs are joined, such as by stitching, 81, in FIG. 7 to form the protector 20.

As shown in FIG. 1 leg protector 24 and calf protector 28 also have respective boot-like portions 82, 84, and have respective joints 86, 88, such as separable joints, using Velcro for example, seamed joints, zippered joints, or the like, as required.

As shown in FIG. 4, arm 34 can move in a lateral direction 90 relative to the top surface 44 and can move in a rotary direction 92. Mat 14 can also move in a lateral direction 94 and a rotary direction 96.

Fabrics 48, 46 of mat 14 typically are identical to respective fabrics 64, 66 of elbow protector 20.

First fabric 64 is a non-woven material similar to that employed by the Colgate-Palmolive Company in its trademarked product HANDI-WIPES. The Kendall Co. of Boston, Mass. supplies this material to companies such as its parent, Colgate-Palmolive. Kendall's product numbers for nonwoven material used by applicant are its #14-6044 and SP 283-7 available from its nonwoven fabric group in Athens, Ga. It is a porous material permeable to air and water which is soft and pliable and typically non-irritating to the skin. It is also moisture absorbent. It is easily folded and compacted which permits ready storage of the composite fabric device for subsequent use.

The second fabric 66, typically a woven, synthetic material, is relatively frictionless when rubbed against itself. For example, a polyester sheer, nylon curtain fabric has been used by the applicant. However, to further reduce the cost, the second fabric can be a "slippery" plastic sheet material. The second fabric material typically is also thin and pliable, permitting easy folding of the composite fabric device, if desired.

First fabric 64 is fixedly secured to second fabric 66, as, for example, by a plurality of stitchings 73, typically repeated over the length of the combined material.

Figure 2:
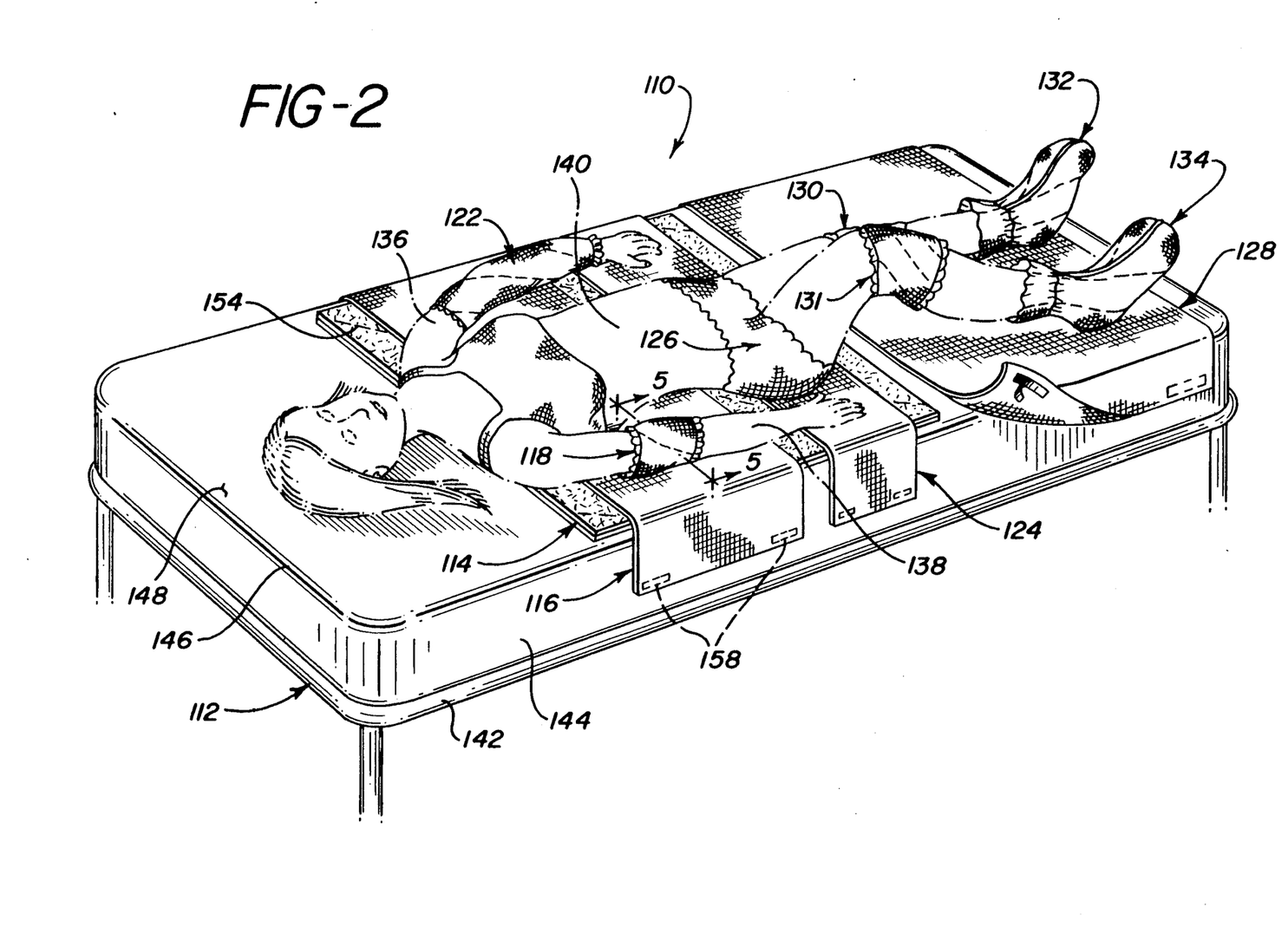
FIG. 2 is a perspective view of additional fabric body protecting means.

As shown in FIG. 2, a second set of embodiments or assembly 110 is provided. Assembly 110 includes a support 112, a two-layer mat 114, an upper frictionless sheet or strip 116, a right elbow protector 118, an upper torso protector 120, and a left arm protector 122. Assembly 110 also includes a middle frictionless sheet 124, and a lower torso protector 126. Assembly 110 also includes a lower frictionless sheet 128, left and right knee protectors 130, 131, and left and right foot protectors 132, 134. A patient rests her left and right arms 136, 138, and her torso 140 on support 112.

As shown in FIG. 2, support 112 has a bed frame 142, a mattress 144, and a cover 146 which has a top surface 148.

Figure 5:
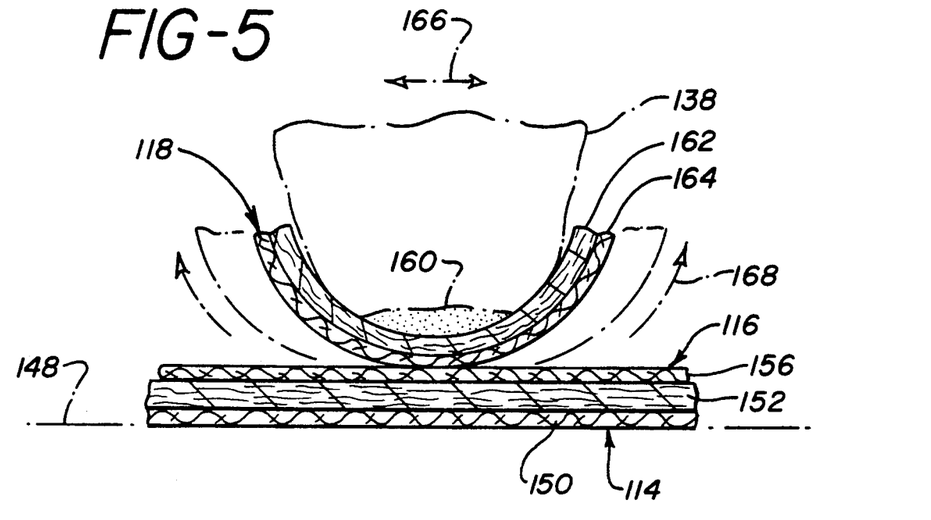
FIG. 5 is a section view as taken on line 5—5 of FIG. 2.

As shown in FIG. 5, mat 114 has a bottom frictionless fabric 150 and a top non-woven fabric 152. Diagonal stitching 154 secures fabric 150 to fabric 152 (see FIG. 2).

Upper frictionless sheet 116, which is identical to middle frictionless sheet 124 and to lower frictionless sheet 128, includes a frictionless nylon fabric 156 and a plurality of connecting means 158, such as double-sided adhesive strips.

As shown in FIGS. 2, 5, 9, 10, 11, and 12, elbow protector 118 is substantially identical in construction to protectors 122, 130, 131, and is similar in construction to protectors 120, 126, 132, 134. Elbow protector 118 covers a sore 160 on the right arm 138. Protector 118 has a first inner non-woven fabric 162 and has a second outer frictionless or nylon fabric 164.

As shown in FIG. 5, arm 138 can move in a lateral direction 166 and in a rotary direction 168 without rubbing, and thus irritating sore 160. Similarly, each of the protectors 118, 120, 122, 126, 130, 131, 132, 134 can move in a lateral direction and in a rotary direction without rubbing against respective covered skin areas or sores.

Figure 9:
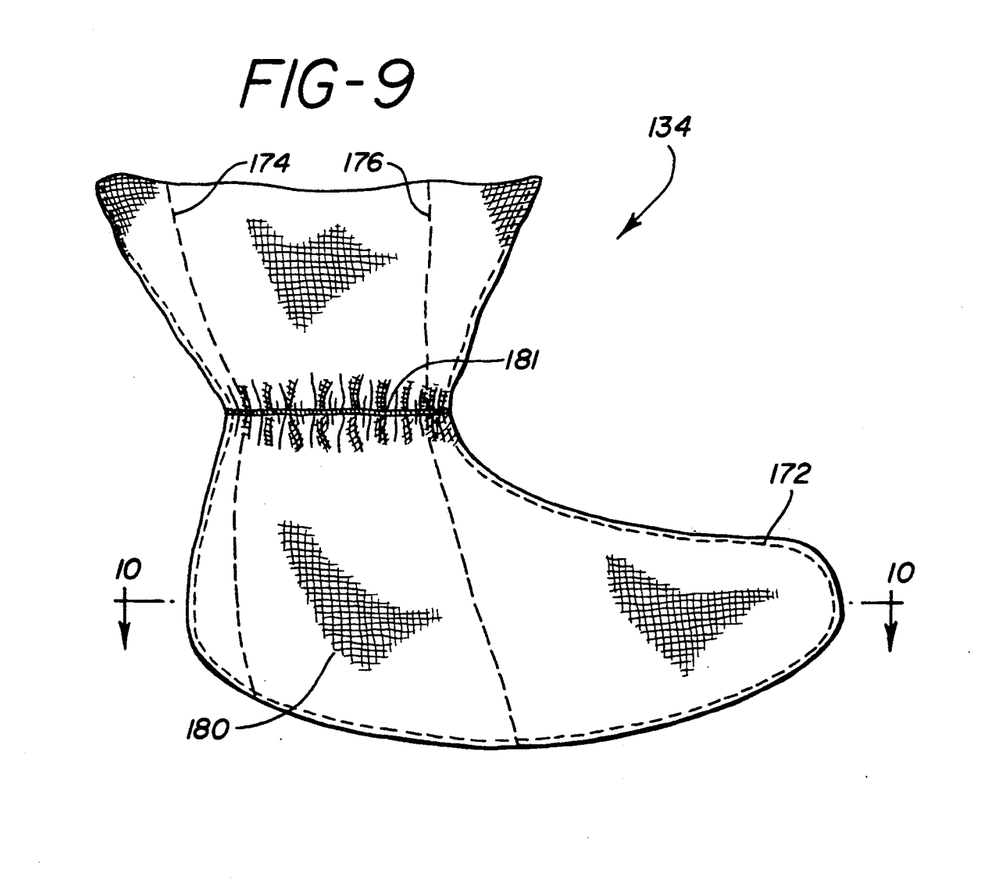
FIG. 9 is an elevation view of a foot protector as shown in FIG. 2.
Figure 10:
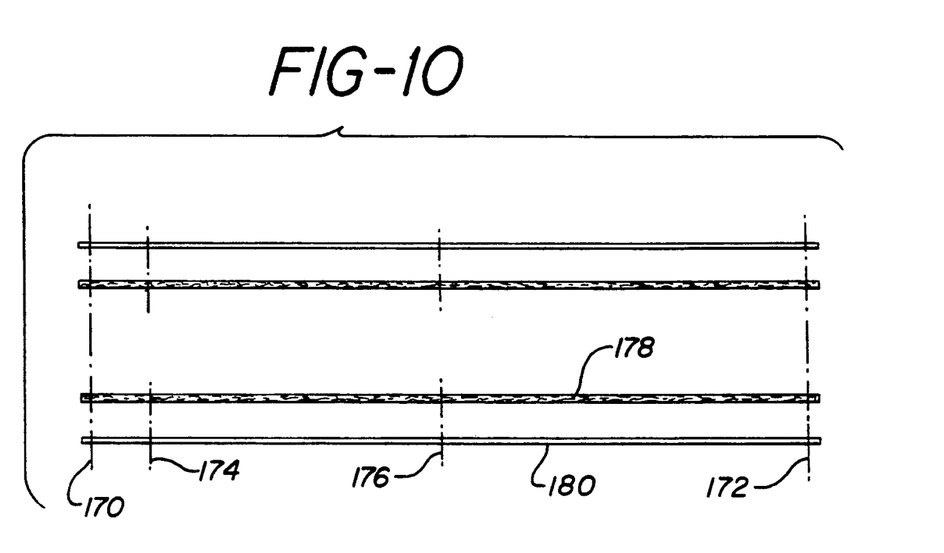
FIG. 10 is a schematic section view as taken on the line 10—10 of FIG. 9.

As shown in FIGS. 9 and 10, right foot protector 134, which is identical to left foot protector 132, has left and right edge stitchings 170, 172. Protector 134 also has inner stitchings 174, 176 which join fabric 178 to fabric 180, on each side thereof. Protector 134 also has an elastic band 181, stitched into the protector approximately above the ankle location used to retain the protector on the foot.

Figure 11:
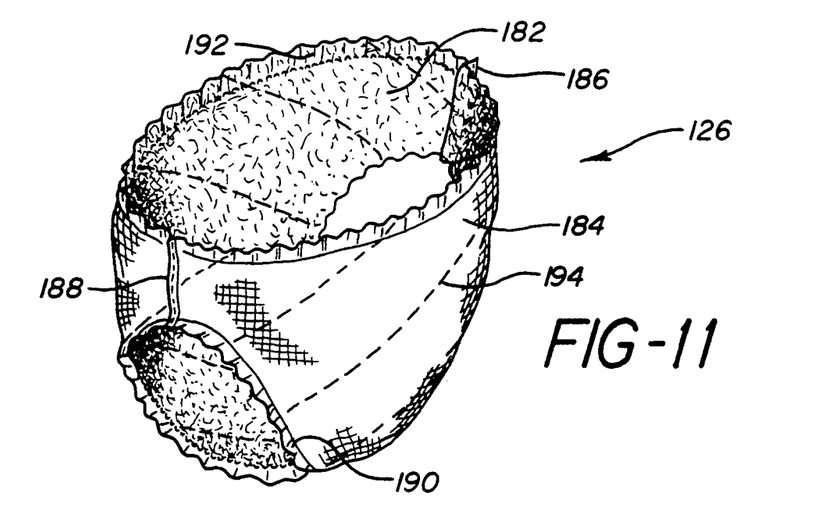
FIG. 11 is an enlarged perspective view of a protector in FIG. 2.

As shown in FIG. 11, middle torso protector 126 has an inner non-woven fabric 182 and an outer frictionless fabric 184 and has seams 186, 188. Protector 126 also has bottom and top elastic bands 190, 192 and diagonal stitching 194.

Figure 12:
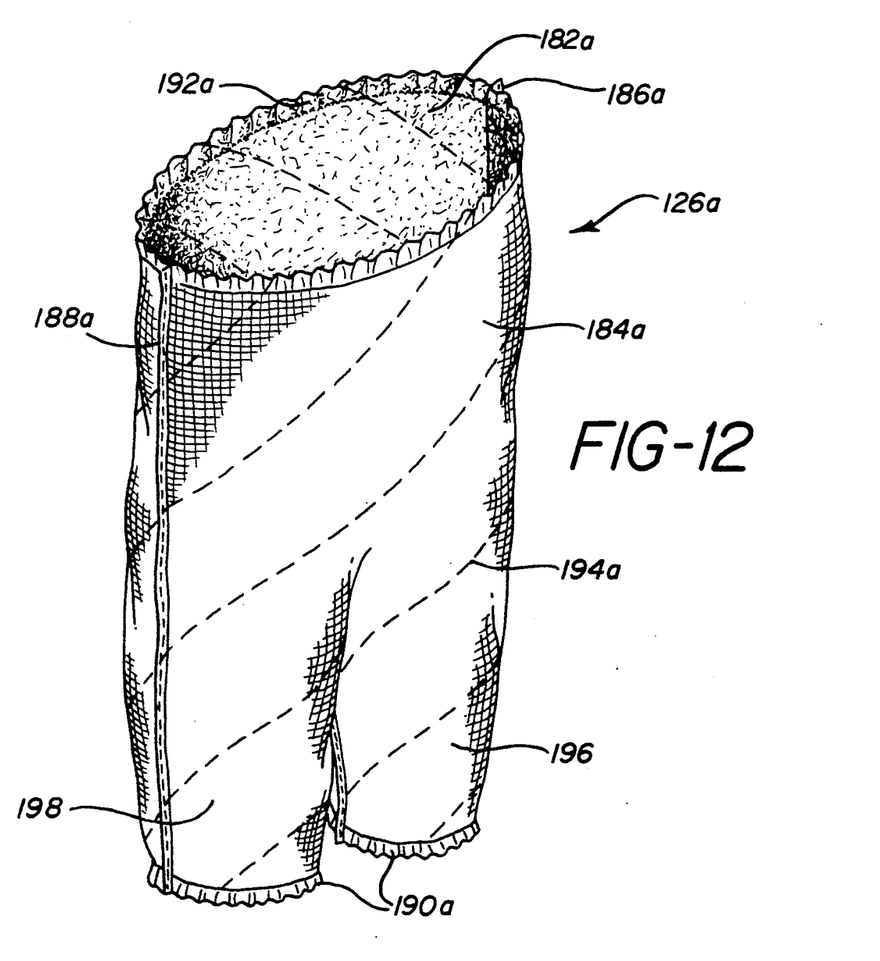
FIG. 12 is an enlarged perspective view of a protector similar to FIG. 11.

As shown in FIG. 12, mid torso to thigh protector 126a is provided. Parts of protector 126a, which are the same as parts of lower torso protector 126, have the same numerals, but with a subscript "a", added thereto. Protector 126a has an inner non-woven fabric 182a, an outer frictionless fabric 184a, seams 186a, 188a, bottom and top elastic bands 190a, 192a, and diagonal stitching 194a. Protector 126a also has elongate thigh portions 196, 198.

Figure 3:
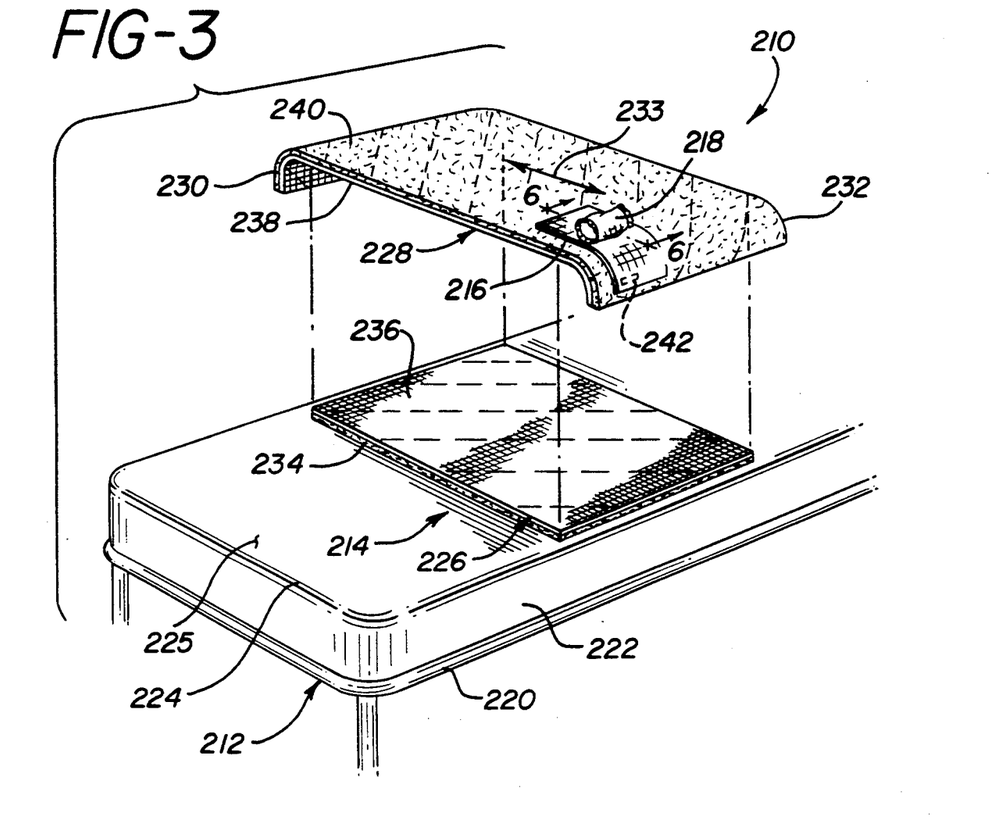
FIG. 3 is a perspective view of an additional fabric body protecting means.

As shown in FIG. 3, a third set of embodiments or assembly 210 is provided. Assembly 210 includes a support 212, a mat 214, a frictionless strip or sheet 216, and an elbow protector 218. Support 212 has a bed frame 220, a mattress 222, and a cover 224 which has a top surface 225.

Mat 214 has a first bottom fabric device 226, and a second top fabric device 228, which typically has left and right curved end portions 230, 232. Top device 228 can move in a lateral direction 233 relative to bottom device 226. Bottom device 226 has a bottom non-woven fabric 234 and a top frictionless fabric 236. Top device 228 has a bottom frictionless fabric 238 and a top non-woven fabric 240. The construction and operative purpose of mat 214 is described in the aforementioned patent.

Frictionless sheet 216 has a plurality of connecting means 242, such as two-sided adhesive tape strips, which connect to fabric 240.

Figure 6:
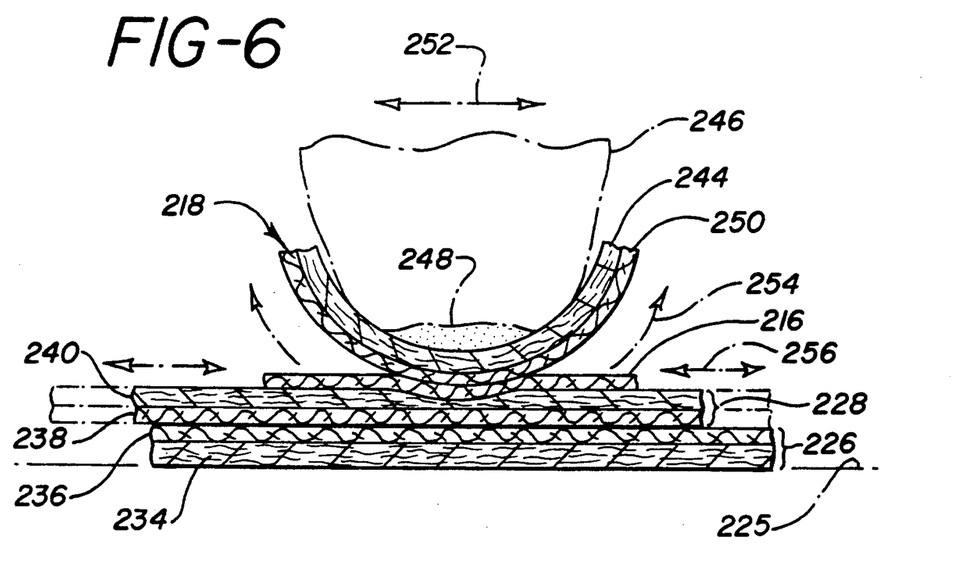
FIG. 6 is a section view as taken on line 6—6 of FIG. 3.
Figure 7:
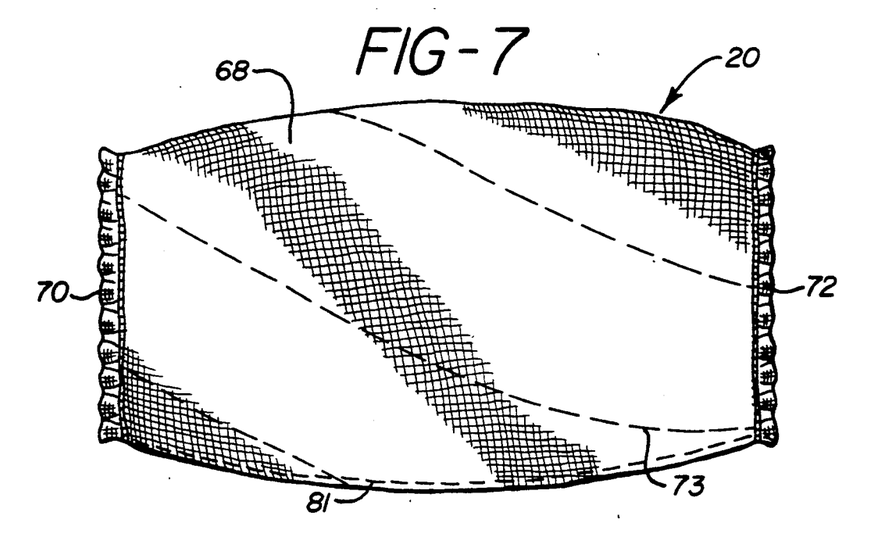
FIG. 7 is a plan view of a fabric elbow protector.

As shown in FIG. 6, elbow protector 218 has a first arcuate inner non-woven fabric 244, which contacts an arm 246 with a sore 248. Protector 218 also has a second arcuate outer frictionless or nylon fabric 250, which contacts frictionless sheet 216.

Arm 246 and protector 218 can move in a lateral direction 252 and in a rotary direction 254 relative to sheet 216 without rubbing the sore 248. Combined fabric device 228 with sheet 216 secured thereto, can move relative to bottom fabric device 226, in a lateral direction 256. Because of the frictionless interface between sheet 216 and outer frictionless fabric 250, this lateral or rotational movement is not experienced by the sore 248 and thus it is not further aggravated.

In principle, what appears to happen when the above described protectors are used in conjunction with a coacting frictionless sheet, is that the skin, sore or wound on the covered body member is isolated from the lateral or rotational movement of the covered body member. The non-woven, soft, pliable material which is immediately in contact with the skin, sore or wound, remains fixed in relation to the contacted area so that the contacted skin does not experience the frictional effects of fabric material passing across it. Thus, no sores are developed; nor existing sores or wounds exacerbated. Further, ointments and salves, such as 62 in FIG. 14, remain concentrated at the point of the area to be treated.

Certain advantages of body portion protecting means, including protectors 18, 20, 24, 26, 28, 118, 120, 122, 126, 130, 131, 132 and 134 are indicated hereafter.

A) The invention is useful for avoiding frictional effects directly on corresponding body areas or sores at an extremity or local body pressure or contact point.

B) Bed sores can be more easily healed by avoiding the exacerbating effects of frictional movement thereto.

C) The invention can be adapted to accommodate a situation where the user is in a sitting position in a chair, car or similar environment.

D) The invention as described can be used in conjunction with the user facilitating device of my aforementioned patent, to provide expanded comfort and convenience to bedridden patients.

As a matter of construction, edge stitchings, such as 81, 86, 88 170, 172, 186 and 188, 186a and 188a, are made to the outside so that they do not become a source of irritation to the user.

Further, as noted above with respect to the leg protector 24 and calf protector 28, any of the protectors can be fabricated having separable, including zippered, joints. This will enable the body portion to be placed thereon and the protector closed around it. This is helpful where it would be painful to slip the protector over the limb or torso to reach the portion to be protected.

An aspect of various embodiments of the present invention, for example, leg protectors 24 and 28, is that they can be used to facilitate the pulling on of an elastic support stocking, a "Jobe" stocking or the like.

The term "frictionless fabric" is used extensively throughout this application. It is understood, of course, that this is used to describe a fabric which is relatively frictionless when rubbed against itself. Typical materials which would fall into this description are identified in my aforementioned patent, U.S. Pat. No. 4,944,053. It is my intention in using the term "frictionless" throughout this specification, to describe that relatively frictionless material described in that patent, or a similar material.

While the invention has been described in various preferred embodiments, it is to be understood that the words which have been used are words of description rather than limitation and that changes may be made within the purview of the appended claims without departing from the true scope and spirit of the invention in its broader aspects.

The embodiments of an invention in which an exclusive property or right is claimed are defined as follows:

1. Body portion protection means comprising:
    (a) a body protector, including
        a first non-woven fabric for contact with a selective body portion; and,
        a second relatively frictionless fabric such that it moves relatively easily on itself, disposed in contact with the first non-woven fabric,
        said body protector formed in a shape so as to envelop a selective body portion; and,
    (b) a third relatively frictionless fabric such that it moves relatively easily on itself, disposed in contact with the second relatively frictionless fabric for allowing said second relatively frictionless fabric to slide freely thereover, thereby minimizing frictional effects on the body portion, said third relatively frictionless fabric disposed upon and extending along a portion of a top surface of a bed, resting surface, or the like.

2. The protecting means of claim 1 further comprising means for connecting selected portions of said body protector whereby said selective body portion is enveloped.

3. The protecting means of claim 2, including
a fourth non-woven fabric in contact with and in support of the third relatively frictionless fabric; and,
a fifth relatively frictionless fabric in contact with and in support of the fourth non-woven fabric said fifth relatively frictionless fabric extending about and nearest the top surface, said fourth and fifth fabric disposed between said third fabric and the top surface of the bed, resting surface of the like.

4. The protecting means of claim 3, including
a sixth relatively frictionless fabric in contact with and in support of the fifth relatively frictionless fabric; and
a seventh non-woven fabric in contact with and in support of the sixth relatively frictionless fabric; said seventh non-woven fabric extending about and nearest the top surface, said sixth and seventh fabric disposed between said fifth relatively frictionless fabric and the top surface of the bed, resting place or the like.

5. The protecting means of claims 2, 3 or 4 wherein the first non-woven fabric is relatively soft, pliable, porous, permeable to air and water, and moisture absorbent and characterized in that it is non-irritating to a person's skin in contact therewith for a prolonged period of time.

6. The protecting means of claim 5, wherein the first and fourth and seventh non-woven fabrics are made from the same material; and
the second and third and fifth and sixth relatively frictionless fabrics are each a nylon material.

7. The protecting means of claim 2 wherein the body portion is a knee.

8. The protecting means of claim 2, wherein the body portion is an elbow.

9. The protecting means of claim 2 wherein the body portion is a foot.

10. The protecting means of claim 2, wherein the body portion is a leg up to the calf.

11. The protecting means of claim 2 wherein the body portion is a leg up to and above the knee.

12. The protecting means of claim 2 wherein the body portion is a torso portion.

13. The protecting means of claim 2 wherein the third relatively frictionless fabric further includes means for connecting to a support surface.

14. The protecting means of claim 4, wherein the fourth and fifth and sixth and seventh fabrics are layers of a mat.

15. The protecting means of claim 14, wherein the mat is a roll-type mat.

16. The protecting means of claim 2, wherein the first and second fabrics have interconnecting stitching and said body portion protector is shaped from flat pieces which are cut from a roll of said stitched first and second fabrics.

* * * * *